United States Patent [19]

Coucke et al.

[11] Patent Number: 5,696,325

[45] Date of Patent: Dec. 9, 1997

[54] APPARATUS FOR TESTING EGGS

[75] Inventors: Peter Marie-Jozef Maurits Willem Coucke, Waregem; Josse Guillaume Philemon De Baerdemaeker, Merchtem; Eddy Marie Paul Decuypere, Haasrode, all of Belgium

[73] Assignee: K. U. Leuven Research & Development, Louvain, Belgium

[21] Appl. No.: 760,135

[22] Filed: Dec. 3, 1996

Related U.S. Application Data

[63] Continuation of Ser. No. 520,267, Aug. 28, 1995.

[30] Foreign Application Priority Data

Aug. 26, 1994 [NL] Netherlands ............... 9401388

[51] Int. Cl.$^6$ .................... G01M 7/00; A01K 43/04
[52] U.S. Cl. ................ 73/595; 73/579; 73/12.13; 209/510
[58] Field of Search .............. 73/595, 579, 12.06, 73/12.12, 12.13, 12.14, 587, 298; 209/510, 511

[56] References Cited

U.S. PATENT DOCUMENTS

| 3,067,605 | 12/1962 | Bliss | 73/595 |
|---|---|---|---|
| 3,503,501 | 3/1970 | Seaborn. | |
| 3,535,912 | 10/1970 | Muller | 73/12.06 |
| 3,744,299 | 7/1973 | Bliss | 73/595 |
| 4,389,891 | 6/1983 | Fournier. | |
| 4,495,792 | 1/1985 | Bai et al. | 73/12.06 |
| 4,801,799 | 1/1989 | Tromborg et al.. | |
| 5,062,296 | 11/1991 | Migliori. | |
| 5,131,274 | 7/1992 | Schouenborg | 73/595 |
| 5,144,838 | 9/1992 | Tsuboi | 73/579 |
| 5,426,977 | 6/1995 | Johnston et al. | 73/595 |

FOREIGN PATENT DOCUMENTS

| 0 295 755 | 12/1988 | European Pat. Off.. |
|---|---|---|
| 61-173157 | 8/1986 | Japan. |
| 62-151749 | 7/1987 | Japan. |
| 4-122853 | 4/1992 | Japan. |
| 91/06211 | 5/1991 | WIPO. |
| 93/17318 | 9/1993 | WIPO. |

*Primary Examiner*—Hezron E. Williams
*Assistant Examiner*—Richard A. Moller
*Attorney, Agent, or Firm*—Banner & Witcoff, Ltd.

[57] ABSTRACT

The invention relates to an apparatus for testing eggs by means of mechanical vibrations, comprising: support means for supporting an egg for testing; an exciter for exciting the egg for testing; a transducer for receiving the vibrations generated in the egg by the exciter and for converting the vibrations into electrical signals; and a measuring instrument connected to the transducer for analyzing the electrical signals coming from the transducer, wherein the exciter is adapted to excite the egg for testing with a single blow.

13 Claims, 2 Drawing Sheets

APPARATUS FOR TESTING EGGS

This application is a file wrapper continuation of application Ser. No. 08/520,267, filed on Aug. 28, 1995.

BACKGROUND OF THE INVENTION

The invention relates to an apparatus for testing eggs by means of mechanical vibrations, comprising: support means for supporting an egg for testing; an exciter for exciting the egg for testing; a transducer for receiving the vibrations generated in the egg by the exciter and for converting the vibrations into electrical signals; and a measuring instrument connected to the transducer for analyzing the electrical signals coming from the transducer.

Such an apparatus is known from the international patent application with publication number WO-93/17318.

In this prior art apparatus excitation of the egg takes place by means of a vibration source, for example a piezoelectric transducer which is brought into contact with the egg, and which sets the egg into vibration at the position of the contact surface between the transducer and the egg. The egg is herein subjected at the relevant location to the vibration at the frequency generated by the transducer. As a result hereof the egg is set into various forms of vibration which can be received by means of a microphone which is arranged on the other side of the egg and which converts the mechanical vibrations of the egg into electrical signals. By means of analyzing the electrical signals, the response of the egg to the mechanical excitation can be measured, at least at the location of the microphone.

Diverse egg characteristics can be determined from this response, such as the fact of whether the egg-shell is whole, i.e. the absence of cracks or holes in the egg-shell, the composition of the contents of the egg, in particular whether the egg is fertilized or not, and perhaps the presence of bacteria, for example salmonella bacteria, in the egg.

The response of the egg to the excitation by this prior art apparatus depends to a large degree however on the frequency of the imposed mechanical vibration signal. This means that only limited information can be obtained from the response signal. Although it is of course possible to carry out the measurements at different frequencies, this requires a larger number of measurements, which takes more time.

BRIEF SUMMARY OF THE INVENTION

The object of the present invention is to provide an apparatus, wherein the above stated drawbacks are avoided.

This object is achieved in that the exciter is adapted to excite the egg for testing with a single blow.

By subjecting the egg to such a pulse-like excitation, the egg is excited with a large number of frequencies; a pulse can anyway be thought of as being composed of a large number of frequencies. As a result the egg is simultaneously excited with a large number of frequencies, so that the response of the egg has many more degrees of freedom, so that the response signals obtained therefrom provide much more information concerning the egg.

The apparatus further relates to a method for testing eggs by means of mechanical vibrations, comprising of mechanically exciting the egg for examining by means of a pulse and measuring the response of the egg.

It is noted here that it is known from a Netherlands patent number 130006 to test an egg by means of exciting the egg with a pulse. A hammer-shaped body is herein caused to fall on the egg, wherein, depending on the fact of whether the egg-shell is intact or damaged, the hammer-shaped body rebounds to a differing degree. The response of the egg is not in fact measured herein, only the degree of resilience of the egg-shell.

BRIEF DESCRIPTION OF THE DRAWINGS

The invention will be elucidated hereinbelow with reference to the annexed drawings, in which.

DETAILED DESCRIPTION OF THE INVENTION

Figure 1:
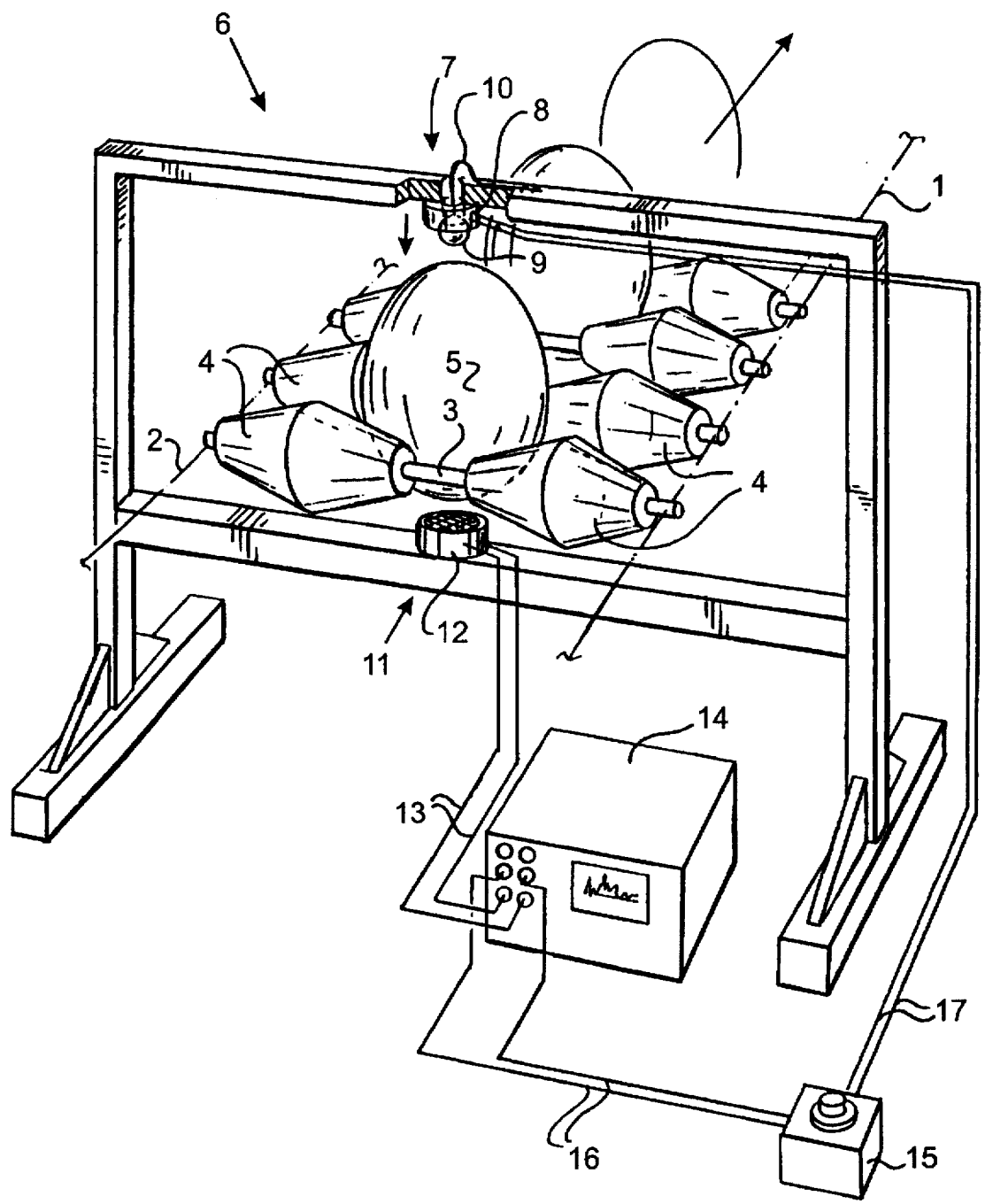
FIG. 1 shows a first embodiment of the invention.

The apparatus according to the invention shown in FIG. 1 comprises two rods 1,2 which extend in horizontal direction, and on which intermediate shafts 3 are arranged at regular distances. Two diabolo-shaped support elements 4 are arranged on each of the intermediate shafts 3. These diabolo-shaped support elements are made of resilient material, for example rubber. As shown in the drawing, an egg 5 can be placed between each set of four diabolo-shaped support elements. When an egg is placed between each set of four support elements, the egg can be carried successively by the horizontal movement of the rods 1,2 to the same position where they can be tested by the testing apparatus according to the invention.

This comprises a frame 6 to which is fixed an excitation element 7 and a microphone 12. The excitation element 7 is formed by an annular electromagnet 8 which is fixed to the frame 6. Underneath the electromagnet 8 is situated a ball manufactured from magnetizable material, for example iron, which, when the electromagnet 8 is switched on, can be pulled toward the electromagnet. To prevent the ball being lost when the electromagnet is switched off, the ball is fixed to the frame by means of a cord 10.

The transducer 11 in the form of a microphone 12 is placed precisely beneath the excitation element 7. The placing of microphone 12 is such that an egg 5 supported by support elements 4 is normally, i.e. when the egg for testing is of normal dimensions, not in contact with the microphone 12.

The microphone 12 is further connected by means of electrical cables 13 to a measuring instrument 14 which can be formed by a device for performing a Fourier analysis, preferably a so-called Fast Fourier analysis. For operation of the apparatus a control button 15 is present which is connected by means of a cable 16 to the measuring instrument 14. The control button 15 is of course also connected to the electromagnet 8 by means of a cable 17.

The operation of the present apparatus will now be described. By means of the rods 2 movable in their lengthwise direction an egg 5 placed on a set of four support elements 4 can be placed under the excitation element 7. When the apparatus is suitable for checking large numbers of eggs, this will of course take place automatically. Automatic apparatus for positioning eggs are known in the prior art.

The egg 5, which is herein placed such that the polar axis thereof coincides as closely as possible with the connecting line between the centre of the excitation element 7 and the microphone 12, is subsequently excited by switching off the normally energized electromagnet 8. The energizing is switched off by pressing the control button 15, whereby the power supply to the electromagnet 8 is temporarily interrupted. The ball 9 hereby drops downward, falls onto the tip of the egg 5 and will move upward due to the resilience of the egg-shell. Pressing the button results in the power supply to the electromagnet being switched off for a short time, so that once the ball has touched the egg, the ball is once again attracted by the magnetic force of the electromagnet 8 which has meanwhile been switched on. The ball 9 is hereby returned to its original location.

The ball 9 has meanwhile caused a pulse-like, mechanical excitation of the egg 5 whereby the egg 5 will, partly depending on the locations where this egg is supported, be set into a large number of different forms of vibration. In amplitude and phase these forms of vibration depend of course on the method of excitation, but also on the thickness of the egg-shell, the fact of whether the egg-shell is undamaged, any damage of the egg-shell in the form of cracks or holes, or on the viscosity and the viscosity in different places of the contents of the egg. This can provide information relating to the freshness of the the size of the yolk, whether or not the egg is fertilized, and possibly the presence of contaminants in the possibly in the form of bacterial contaminants, for example by salmonella bacteria.

The vibrations of the egg will result in sound waves which are received by the microphone 12. It will be apparent that the frequency spectrum and the phase of the signals generated in the microphone by the vibrations of the egg are greatly dependent on the forms and amplitudes of vibration of the egg.

These signals are guided via cable 13 to a measuring instrument 14 which is preferably adapted to carry out a Fourier analysis, for example a Fast Fourier analysis. As a result thereof the frequency spectrum of the vibrations present in the egg can be analyzed. The frequency spectrum is preferably made visible by means of a cathode-ray tube or other display device, although it is likewise possible to have the frequency spectrum printed on paper or stored in electronic form. It is of course possible to analyze the frequency spectrum automatically, for example by checking it against standard values, whereby a quality control of the egg can be carried out automatically. The above-stated qualities of the egg can be determined herewith, such as the fact of whether or not the egg is fertilized, contamination of the egg and so on.

Figure 2:
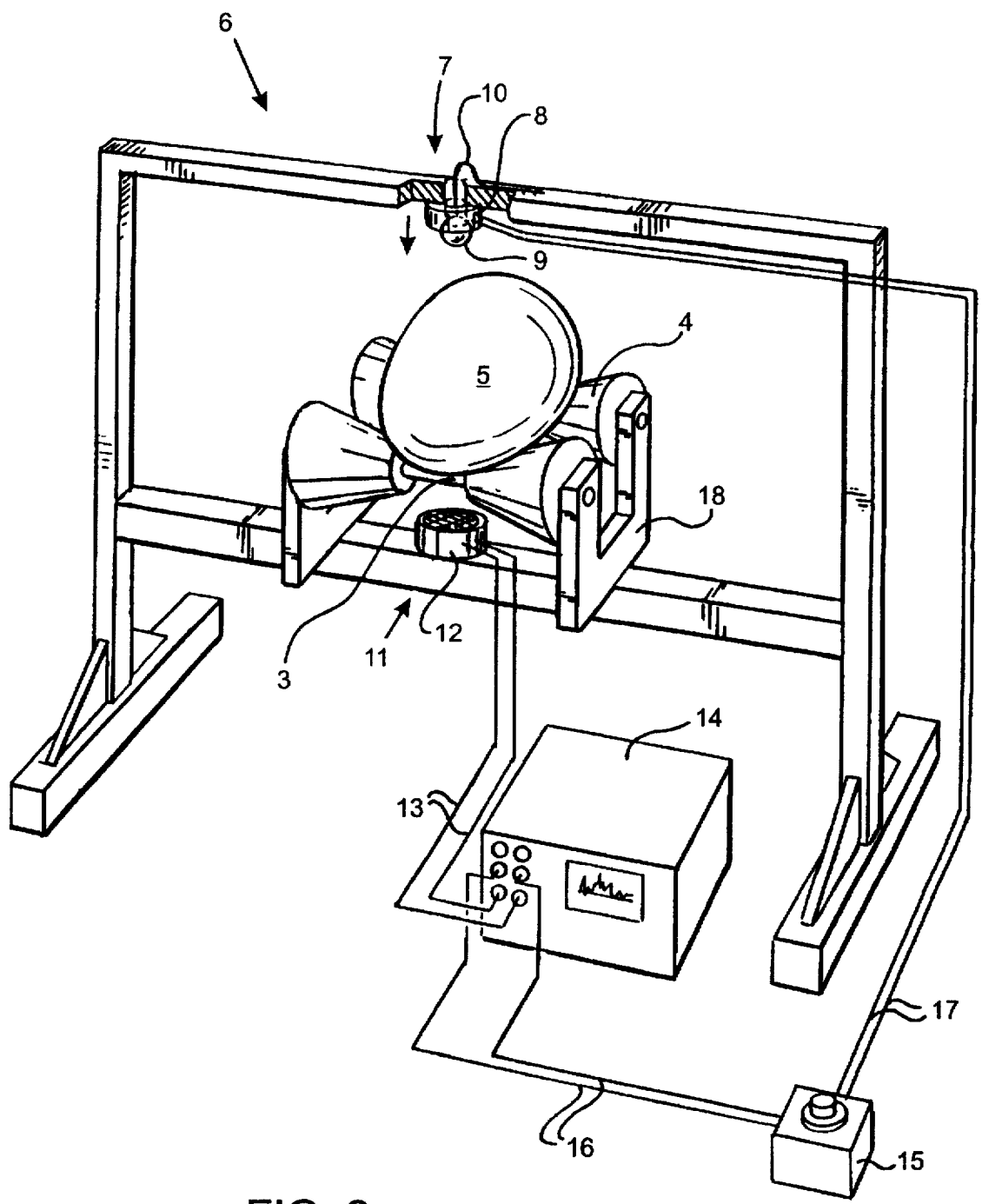
FIG. 2 shows a second embodiment of the invention.

The embodiment of the invention shown in FIG. 2 corresponds with the embodiment shown in FIG. 1, with the understanding that here the egg is rotated through 90°, so that the ball does not strike the tipped or rounded end of the egg but strikes the egg approximately in the centre plane. This results in a different vibration pattern from which other information concerning the qualities of the egg can be derived.

This apparatus differs further in that no transporting means for the eggs is present; there are only fixed support means. These are again formed by diabolo-shaped elements which are mounted on fixed brackets 18.

This latter embodiment is thus particularly suitable for laboratory use and the embodiment shown in FIG. 1 is more suitable for industrial applications.

It is of course possible to vary from the embodiment of the invention shown here; it is thus possible for example to place the microphone at a different location relative to the egg, for example to the side of the egg. It is of course also possible to supply the egg in reverse manner, i.e. not with the tip upward but with the rounded end upward, or to test the egg with the longitudinal axis horizontal. These other orientations of the egg can also be applied with the same placing of the microphone or with a different placing of the microphone. It is of course even possible to use more microphones.

It is however important that a single excitation of the egg takes place and, when it is desirable for more excitations to take place, that the following excitation takes place only after the vibrations caused in the egg by the previous excitation are damped.

We claim:

1. Apparatus for testing eggs by means of mechanical vibrations, comprising:

support means for supporting and egg for testing;

an exciter for exciting the egg for testing by physically contacting the egg;

a transducer for receiving the vibrations generated in the egg by the exciter and for converting the vibrations into electrical signals, said egg being disposed between said exciter and said transducer, wherein said transducer is not in contact with the egg and only receives said vibrations through the space between the egg and the transducer; and a measuring instrument connected to the transducer for analyzing the electrical signals coming from the transducer, wherein the exciter is adapted to excite the egg for testing with a single physical blow.

2. Apparatus as claimed in claim 1, characterized in that the exciter is adapted to excite the egg again after the vibration phenomena of the previous excitation are damped.

3. Apparatus as claimed in claim 1, characterized in that the exciter comprises a body which is movable in vertical direction and adapted to strike the egg.

4. Apparatus as claimed in claim 3, wherein said exciter further comprises an electromagnet, said electromagnet being operative to move said body in said vertical direction, and said body comprising a metal ball.

5. Apparatus as claimed in claim 4, characterized in that the metal ball is connected by a cord to an immobile part of the exciter.

6. Apparatus as claimed in claim 1, wherein said support means are formed by support elements lying in one plane, and a shortest distance between said exciter and said transducer defining a connecting line, said connecting line intersecting said plane.

7. Apparatus as claimed in claim 6, characterized in that the connecting line intersects the plane perpendicularly.

8. Apparatus as claimed in claim 7, characterized in that the connecting line between the center of the exciter and the transducer intersects the center of the egg when the egg is supported for testing.

9. Apparatus as claimed in claim 6, characterized in that the support means are formed by four substantially diabolo-shaped support elements manufactured from resilient material.

10. Apparatus as claimed in claim 9, characterized in that the support elements are arranged in pairs on two elongate carriers, said carriers being displaceable in a lengthwise direction.

11. Apparatus as claimed in claim 1, characterized in that the measuring instrument is adapted to perform a Fourier analysis.

12. Method for testing eggs by means of mechanical vibrations, comprising mechanically exciting the egg for testing by means of a pulse produced by physically contacting the egg and measuring the response of the egg using a transducer that is not in contact with the egg and only receives said response through the space between the egg and the transducer.

13. Method as claimed in claim 12, characterized in that the transducer is a microphone.

* * * * *